(12) United States Patent
Bathe et al.

(10) Patent No.: US 9,659,739 B2
(45) Date of Patent: May 23, 2017

(54) BLANKING OF ELECTRON BEAM DURING DYNAMIC FOCAL SPOT JUMPING IN CIRCUMFERENTIAL DIRECTION OF A ROTATING ANODE DISK OF AN X-RAY TUBE

(71) Applicant: KONINKLIJKE PHILIPS N.V., Eindhoven (NL)

(72) Inventors: Christoph Helmut Bathe, Hamburg (DE); Thorben Repenning, Moorrege (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 158 days.

(21) Appl. No.: 14/399,658

(22) PCT Filed: May 17, 2013

(86) PCT No.: PCT/IB2013/054050
§ 371 (c)(1),
(2) Date: Nov. 7, 2014

(87) PCT Pub. No.: WO2013/175370
PCT Pub. Date: Nov. 28, 2013

(65) Prior Publication Data
US 2015/0098548 A1 Apr. 9, 2015

Related U.S. Application Data

(60) Provisional application No. 61/649,979, filed on May 22, 2012.

(51) Int. Cl.
*H05G 1/34* (2006.01)
*H01J 35/14* (2006.01)
(Continued)

(52) U.S. Cl.
CPC .............. *H01J 35/14* (2013.01); *A61B 6/405* (2013.01); *A61B 6/4021* (2013.01); *A61B 6/54* (2013.01);
(Continued)

(58) Field of Classification Search
CPC .......... H01J 35/14; H01J 35/24; H01J 35/305; H01J 35/30; H05G 1/26; H05G 1/32;
(Continued)

(56) References Cited

U.S. PATENT DOCUMENTS

| 4,145,616 A | 3/1979 | Tanabe |
| 6,178,226 B1 | 1/2001 | Hell et al. |

(Continued)

OTHER PUBLICATIONS

Whittaker, "X-Ray Anode Surface Temperatures: The Effect of Volume Heating", SPIE, vol. 914, Medical Imaging II, 1988, pp. 565-576.

(Continued)

*Primary Examiner* — Thomas R Artman

(57) ABSTRACT

An apparatus (210) and method for total or partial blanking of an electron beam (e) during a jump between the 2 or more positions of a dynamic focal spot (FP) movement in circumferential direction of the electron beam impinging on the focal track (FPTR) of a rotating target disk (230) of a X-ray tube (110). Alternatively the focal spot size can be increased during this short time interval. Overheating of the anode at the focal spot can be prevented.

15 Claims, 5 Drawing Sheets

(51) Int. Cl.
  *H01J 35/30*    (2006.01)
  *H05G 1/46*     (2006.01)
  *A61B 6/00*     (2006.01)
  *G01N 23/225*   (2006.01)
  *H01J 35/24*    (2006.01)

(52) U.S. Cl.
  CPC .......... *G01N 23/2252* (2013.01); *H01J 35/24* (2013.01); *H01J 35/30* (2013.01); *H01J 35/305* (2013.01); *H05G 1/34* (2013.01); *H05G 1/46* (2013.01); *A61B 6/4441* (2013.01)

(58) Field of Classification Search
  CPC .. H05G 1/34; H05G 1/36; H05G 1/46; H05G 1/52; H05G 1/54; H05G 1/30
  See application file for complete search history.

(56) References Cited

U.S. PATENT DOCUMENTS

| | | |
|---|---|---|
| 7,496,180 B1 | 2/2009 | Subraya et al. |
| 2008/0043916 A1 | 2/2008 | Lemaitre |
| 2010/0008470 A1 | 1/2010 | Hauttmann et al. |
| 2010/0172475 A1 | 7/2010 | Behling |
| 2011/0038460 A1 | 2/2011 | Grasruck et al. |
| 2011/0142193 A1 | 6/2011 | Frontera et al. |
| 2011/0280376 A1 | 11/2011 | Behling et al. |
| 2012/0045036 A1 | 2/2012 | Morton et al. |

OTHER PUBLICATIONS

Lounsberty et al, "New CT Tube Performance Specification", Physics of Medical Imaging, Proceedings of SPIE, vol. 5368, 2004, pp. 621-632.

BLANKING OF ELECTRON BEAM DURING DYNAMIC FOCAL SPOT JUMPING IN CIRCUMFERENTIAL DIRECTION OF A ROTATING ANODE DISK OF AN X-RAY TUBE

CROSS-REFERENCE TO PRIOR APPLICATIONS

This application is the U.S. National Phase application under 35 U.S.C. §371 of International Application Serial No. PCT/IB2013/054050, filed on May 17, 2013, which claims the benefit of U.S. application Ser. No. 61/649,979, filed on May 22, 2012. These applications are hereby incorporated by reference herein.

FIELD OF THE INVENTION

The present invention relates to an apparatus for controlling an X-ray tube with shiftable focal point capability having a movable anode, to a method of controlling an X-ray tube with shiftable focal point capability having a movable anode, to an x-ray tube, to a medical x-ray imager, to a computer program element, and to a computer readable medium.

BACKGROUND OF THE INVENTION

Some medical X-ray imagers have X-ray tubes with rotating anode disks and a further dynamic feature that allows changing by means of electric or magnetic fields the direction of the electron beam incident on the rotating anode. This dynamic focal spot movement helps increase image quality, that is less noise and higher resolution are achievable without increasing power or decreasing focal spot size. However it has been observed that such imagers require frequent maintenance when run at relatively high tube power. An imager with a rotatable anode is described in US 2011/0280376.

SUMMARY OF THE INVENTION

There may therefore be a need for an apparatus that enables more efficient use of said X-ray imagers.

The object of the present invention is solved by the subject matter of the independent claims wherein further embodiments are incorporated in the dependent claims.

It should be noted that the following described aspects of the invention equally apply to the method of controlling an X-ray tube with shiftable focal point capability having a movable anode, to the X-ray tube, to the medical x-ray imager system, to the computer program element and to the computer readable medium.

According to one aspect of the present invention there is provided an apparatus for controlling an X-ray tube with shiftable focal point capability having a movable anode, the focal point (also referred to as "focal spot") formed by an electron beam incident on the anode at that point, comprising:

a focal point shift registering unit for registering a focal point shift across the anode, the shift occurring along a trajectory traced out by the shifting focal point across at least part of the moving anode;

an electron beam mitigator configured to mitigate, in response to the focal point shift so registered, the incident electron beam electron beam whilst the shifted focal point traces out its trajectory across the moving anode. The mitigation action is dependent on the relative velocity between the focal point and the anode.

The apparatus may be put to use in X-ray imagers having X-ray tubes with rotary anode disks where the electron beam is made to "jump" by means of electric or magnetic fields between at least two positions in circumferential direction of the rotation. Although this dynamic focal spot movement allows increasing image quality (less noise and higher resolution) without increasing power or decreasing focal spot size, an adverse effect of this feature has been observed. The dynamic focal point shift may be directed in radial direction of the anode disk or it may be directed into the circumferential direction of the anode disk (rotation) or a combination thereof. The relative velocity between focal point and anode surface is the vector sum of the velocity components of i) the shifting focal point (caused by the electron beam changing direction) trajectory and ii) the motion of the anode disk. A drop in relative velocity occurs in particular at instances where both the velocity components are parallel that is, both, are pointing in the same direction. More specifically and according to one embodiment, the motion of the anode disk is a rotation and the focal point trajectory is along a line essentially across the outer rim of the disk, so is tangential to the rotational velocity of the disk. In this embodiment the velocity decreases whilst the focal point travels or shifts on its straight trajectory in the direction of the anode disk's rotation. At these instances (and/or points) of lower velocity or even zero velocity a high anode surface temperature has been observed. This temperature surge leads to X-Ray dose output degradation because of roughening of focal track and arcing due to evaporation of focal track material. In particular, the negative effect of focal point shift in the direction of the rotation on dose degradation has been noted. So, although focal point shifts help increase image quality, the focal point shift's velocity components in rotation direction may in practice mean a shorter tube lifetime when focal point shift is used or a reduced power specification for a given tube design must be used when focal point shift x-ray tube's lifetimes are not to be reduced.

The proposed apparatus helps secure the advantages of the focal point shift feature without compromising power specification and tube lifetime because the electron beam is mitigated as soon as the apparatus's registration unit registers focal point shift in rotation direction and said mitigation is maintained throughout the focal point shift in that direction.

Handling of situations where more complex electron beam and/or dynamics are involved is also contemplated where the anode and/or focal point travel along more involved curvilinear paths. In this embodiment registration unit is configured to pick up those instances where the velocity components are parallel and then instructs mitigator to commence and maintain beam mitigation upon and throughout such critical instances to keep temperature surges on anode disk's surface at bay.

During the x-ray imager duty cycle, "useful" projection images are obtained. The duty cycle projection images are useful because they are actually used in a tomographic reconstruction of the slice image. The useful images are obtained whilst the electron beam is stationary, that is, it is not changing direction. This situation is in contrast with the "unusable" projection image exposures obtainable during the focal point jump or change of the electron beam's direction. Because temperature bursts on the focal point track caused by even instantaneous parallel alignment of a focal point velocity component and anode rotation velocity component are eliminated, the apparatus allows maximizing the capabilities of rotational anode X-ray scanners with shiftable focal point by increasing lifetime of the x-ray tube and at the same time allows operating the tube at maximum power during the imager's duty cycle.

According to one embodiment, mitigation action commences upon registration of a drop in the relative velocity below a threshold value.

According to one embodiment, the mitigation action remains effective until the relative velocity rebounds to or exceeds the threshold value.

According to one embodiment, X-ray mitigator acts so as to avoid an increase of temperature at the focal spot above a critical temperature threshold whilst the focal point is shifting.

According to one embodiment, the trajectory describes an oscillation of the focal point between two rest positions on the anode, the mitigation action remaining effective for a time period about 1-20% or more particularly about 10% of a residence time of the focal spot at either one of the two rest positions.

According to one embodiment, the mitigation action includes blanking out the electron beam to so avoid the electron beam reaching the anode, the blanking effected, in particular, by using a grid switch technology.

According to one embodiment, the mitigation action is partial blanking and includes reducing the electron beam power as a function of the square root of the ratio between i) the minimum relative velocity of the focal point during the shift and ii) the average velocity of the anode movement.

According to one embodiment, the mitigation action includes increasing size or area of the focal spot.

According to one embodiment, the mitigation action includes increasing at least one of a length of the focal spot perpendicular to (or, for the case of anode rotation, radial to) the focal point track and a width of the focal spot along (tangential) to the focal point track as a function of the ratio or the square root of the ratio between i) the average velocity of the anode movement and ii) the minimum relative velocity of the focal point during the shift. In one embodiment, both, length and width are increased according to said function. In this embodiment the increase in focal spot size/area is so as to just off-set for a decrease in relative (tangential to the rotation or focal track) focal point velocity so to substantially prevent the anode temperature to increase and still maintain a relatively small focal point. However in other, simpler, alternative embodiments, the focal spot size/area can be increased by a smaller or larger, fixed or a random (within reasonable margins) amount in either or both dimensions.

In short, the proposed apparatus effects total or partial blanking of the electron beam during the time needed for jumping between the 2 or more positions of a dynamic focal spot movement in circumferential direction of the electron beam impinging on the focal track a rotating target disk of a X-ray tube with the aim to prevent overheating of the focal spot material. Alternatively to (or in conjunction with partial blanking) blanking, the focal spot size can be increased during this short time interval.

Definitions

The term "mitigation" is meant to include actions that lessen intensity or make the electron beam less acute when impacting on the anode disk. Mitigation as understood herein includes in particular blanking, partial blanking, switching off the cathode and enlarging the area of the focal point (thereby reducing the power density at that point) when incident on the anode surface.

The term "blanking" is meant to include manipulations or control actions on or in the X-ray tube that substantially prevent or inhibit the electron beam from reaching the anode without switching off x-ray power supply.

The term "partial blanking" is a relaxation of "blanking" in that it includes control actions on or in the X-ray tube that result in reducing the number of electrons per unit time to reach the anode and does include in particular reducing X-ray power.

The term "focal point track" is the focal point's path traced out on the anode due to the anode's motion, in particular its rotation.

The term "focal point trajectory" is the path between at least two rest points, the path traced out by the electron beam changing direction.

The term "rest point(s)" include point(s) on the focal point trajectory where the electron beam is stationary but also includes points where on the trajectory where there is no velocity component in the direction of the anode motion, for example purely radial motion of the focal point along the anode.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
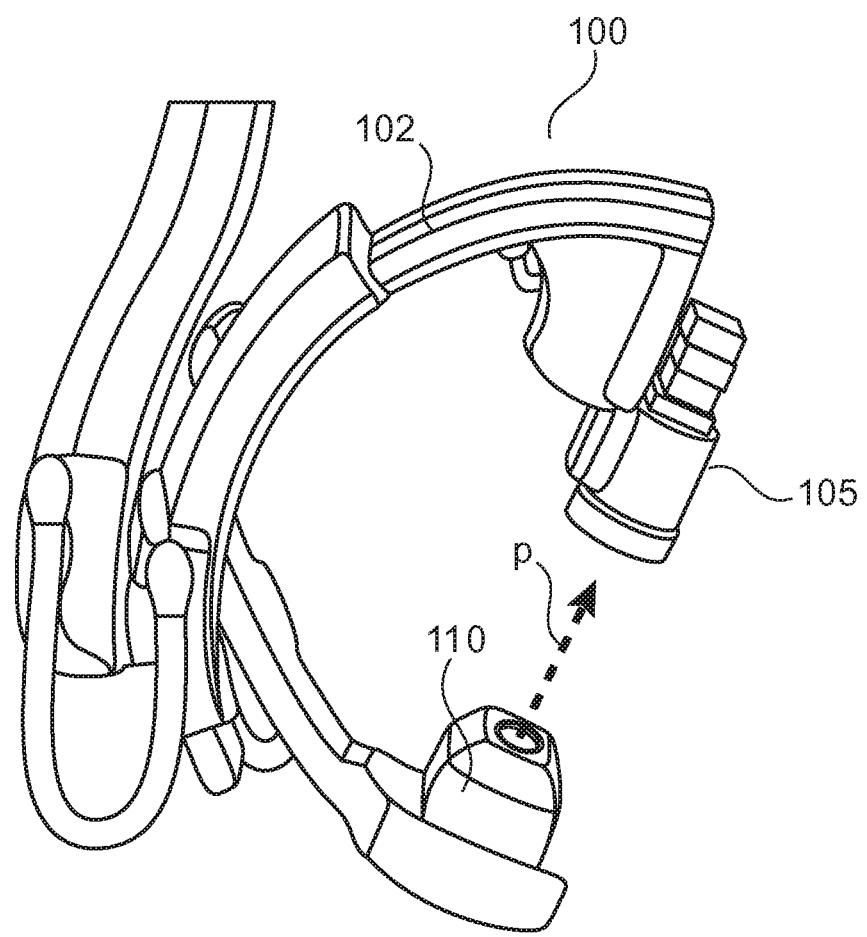
FIG. 1 shows an x-ray imager with an x-ray tube.

With reference to FIG. 1 there is shown an x-ray imager having a rigid gantry 102 to which are attached in opposing relationship an x-ray sensor 105 and an x-ray tube 110. FIG. 1 shows x-ray tube 110 and detector 105 in their respective outer housings or shells. X-ray 110 projects a beam of x-rays p towards detector 105. In FIG. 1 the imager is of a "C-arm" type but it is understood that the following is equally applicable to other x-ray imagers having different constructions.

Figure 2:
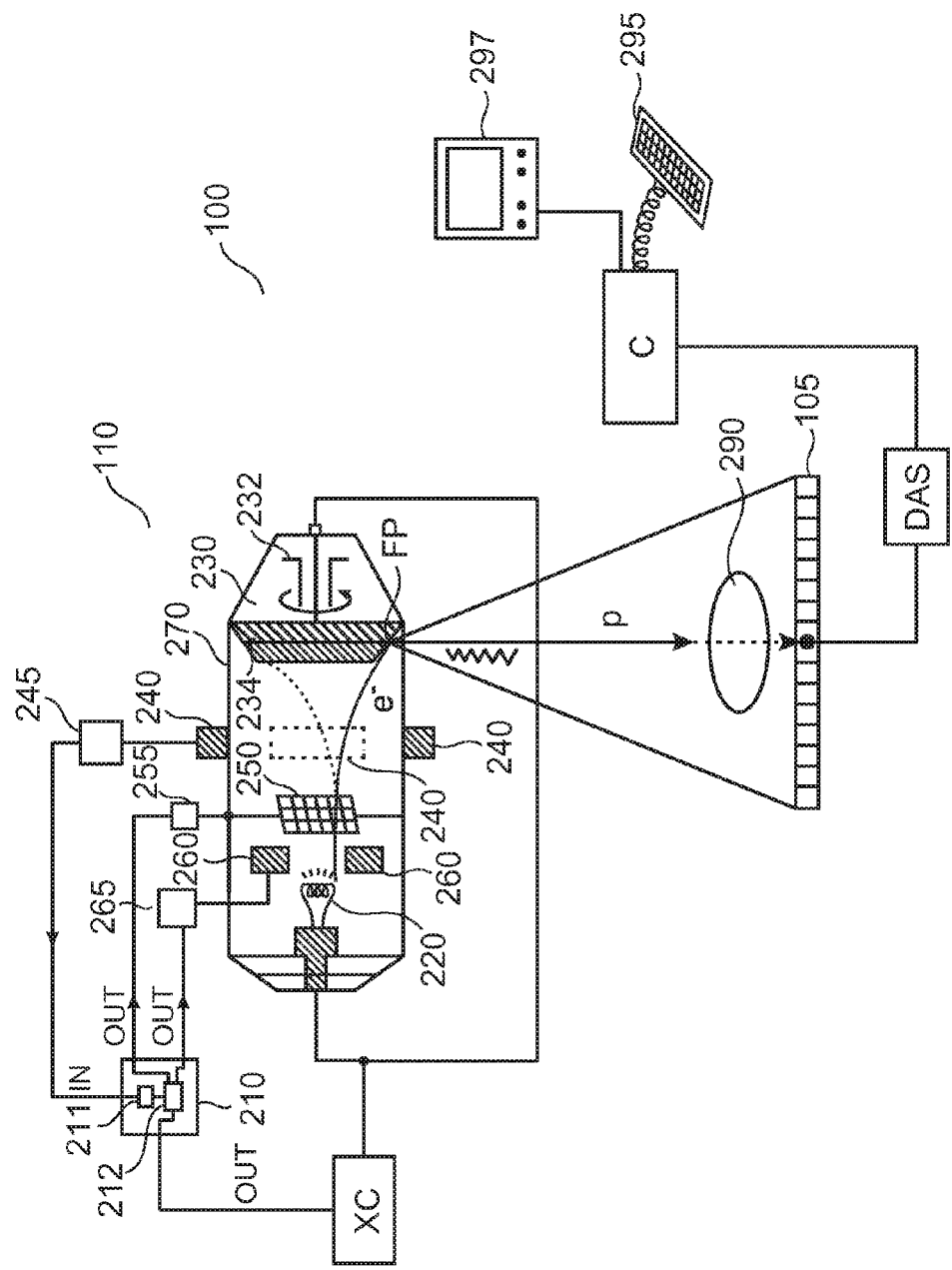
FIG. 2 is a more detailed view of the x-ray tube of FIG. 1 and a controller as proposed herein.

FIG. 2 shows in more detail certain components of the x-ray imager 100 in FIG. 1 in particular x-ray tube 110. X-ray tube 110 is arranged to emit x-ray p which are attenuated by tissue of an object 290 for example a patient undergoing examination whilst residing on an examination table interposed between X-ray tube 110 and detector 105. The attenuated x-ray (shown in FIG. 2 in dashed lines) interacts with detector cells of detector 105. The interaction is translated into digital signals by a data acquisition system DAS and the projection image so obtained is stored on a central computer system C. Gantry 102 is rotatable in a plane around the patient so a series of different projection images at different projection directions are acquired from object 290. Computer C runs image reconstruction algorithm which reads in the series of projection images and produces a slice image showing a cross section through the anatomy of object 290 in the rotation plane in which gantry 102 rotates around body 290. Computer C is connected to an operator console 295 which allows operation by an operator of the imager 100. The reconstructed slice images can then be viewed on likewise connected screen 297.

Operation of X-ray 110 will now be explained in more detail with further reference to FIG. 2.

X-ray tube comprises, within a vacuum tube housing 270, a cathode 220 and an anode 230 positioned at a distance from said cathode 220. Anode 230 is rotatable in a bearing 232 and comprises an anode disc 234. An x-ray controller XR is configured to issue power and timing signals to x-ray tube 110. In particular, a high voltage U is applied across cathode 220 and anode 230. Electrons are emitted as an electron beam e- from cathode 220 and are accelerated towards anode 230 by the electro-motive force provided by voltage U. Accelerated electrons gain high kinetic energy, the plurality of electrons so accelerated forming an electron beam e- which impacts on anode disc 234. The electrons undergo deceleration upon impact and the net kinetic energy is then released as x-ray beam p which egresses vacuum tube housing 270 and then passes through object 290 as shown in FIG. 2 and explained above. Anode disk 234 is beveled at its outer rim so that x-ray beam p can be deflected off anode disk 234 at a desired angle thereby facilitating egress of x-ray beam p.

Anode disc 234 carries a coating on the side the electron beam is incident. The coating is formed from material, for example tungsten, which renders the disc 234 fit for purpose as disc 234 is exposed to high thermal mechanical wear and tear due to the incident beam of high energy electrons. The anode disc 234 and in particular its coating is gradually whittled away as the electron beam impacts same, causing anode disc material sputtering and even evaporation of same. The wear on the disc 234 can be alleviated by rotating it (as shown in FIG. 2) during exposure to the electron beam. The impacting electron beam has a certain cross section which is shown in an idealized manner in FIG. 2 as a line. Impacting electron beam on the disc defines a focal point FP (or focal spot) having width W and length L. Rather than having the electron beam impact disc 234 at a single point at all times, the disc rotates thereby by spreading the wear across the surface of the disc. While the disc is rotating the focal point FP traces out an apparent focal track FPTR across the coated anode disc surface.

X-ray tube 110 further comprises magnetic or electrostatic focusing elements 260 controlled by a suitable controller (or driver) 265. Focusing elements 260 help focus the electron beam on the anode disc 234.

There is further arranged in the tube deflection elements 240 controlled by controller (or driver) 245. Deflection elements 240 and their controller 245 form in essence a focal point shifter that allows changing direction of electron beam thereby shifting the focal point FP across the surface of anode disc 234.

The deflection elements 240 are arranged to encircle the electron beam, with one on bottom, one on top and one on each side (indicated in side elevation by dashed lines in FIG. 2). In one embodiment, the deflection elements are electromagnets selectively energized by controller 245 so that deflection along x/-x and or z/-z directions can be effected to thereby make the electron beam trace out its trajectory on the anode disk's 234 surface. In another embodiment deflection affects electrostatically the deflection element 240 comprising suitably arranged wiring to build up corresponding electric fields with each of the desired orientations.

The effect of focal point shifter will now be explained in more detail below with reference to FIG. 3. There is shown a schematic view on anode disc 234 in the direction of the incident electron beam. To the left there is shown the situation in a conventional x-ray tube without shiftable focal point fp capability. To the right there is shown the situation in an x-ray tube of FIG. 2 having a focal point shift capability. Focal point FP's cross section is diagrammatically shown as rectangular but this may not be so. Focal point FP cross-section can assume any shape. The rotatable anode disc 234 defines two orientations, namely radial direction Z and tangential (to the rotation) direction X. Focal point FP's width W and length L can be respectively defined, one for each direction so focal point FP can be said to have width and length. Focal point FP defines the area of points on the rotating disc that are exposed to the electron beam at the same time. Focal point shifter 245/240 is operative to shift the focal point from one rest position P1 to another rest position P2 across a focal point trajectory FPT. The Positions of rest points P1 and P2 are defined by means of a non-rotating fixed co-ordinate system. Dashed line shows the focal point track FPTR that is traced out as anode moves relative to the beam when the FP is in either one of the rest points P1, P2. According to one embodiment, rotatory anode causes the focal point track FPTR to assume the shape of a circle as indicated in dashed lines in FIG. 3. However, other configurations are contemplated in which the motion of the anode (which may or may not be a disk) is not a rotation but can be any type of motion in which case the focal point track may assume other curvilinear shapes or may be as simple as an oscillation along a linear line.

Figure 3:
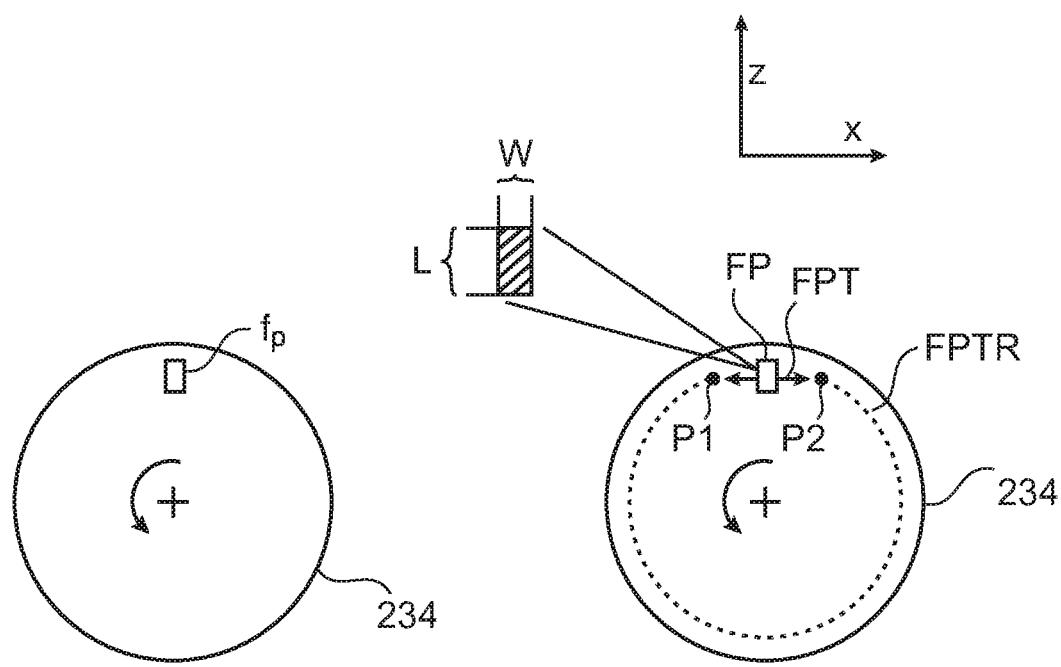
FIG. 3 is a view on an anode disk as used in the x-ray tube of FIG. 2.

According to one embodiment and as shown in FIG. 3, focal point FP oscillates between the two rest points P1 and P2 and resides at either one of them for a short period of time called the residence time RT. Focal point trajectory FPT is traced out during transition time that is during the action of the focal point shifter 245/240 when focal point moves from rest position P1 to position P2 or vice versa. In the geometry shown in FIG. 3 the relative motions of velocities of the focal point shift and the anode rotation are essentially superposed thereby giving rise to a relative velocity v between the focal point FP and the anode disc surface which is given by the vector sum of the respective at least instantaneous velocity components. In the specific example in FIG. 3 the focal point trajectory FPT is a straight line that is traced out circumferentially or tangential to the rotation of the disc 234, that is, tangential to the circular focal point track. In other words when the focal point is shifted from P2 to P1 ("P2→P1") the respect velocity components are parallel (that is the vector components are geometrically parallel and they have the same direction) whereas when the focal point shifts from P1 to P2 ("P1→P2") the velocity components are anti-parallel (that is, the vector components are geometrically parallel but have opposite directions). In x-ray tubes 110 with shiftable focal point capability, the imager delivers higher image quality (for a given tube power level and focal spot size), that is, there is less image noise signals in high image resolution without increasing power or decreasing focal spot size.

The electron beam impacting by impinging at focal point FP on disc 234 causes anode surface temperature Tfs at that point to increase proportionally according to:

$$Tfs \sim \frac{P}{L} * \sqrt{\frac{1}{B*v*cp*\mu}} \quad (1)$$

wherein:
P power of electron beam;
L focal spot length in radial direction of anode disk;

B focal spot width in circumferential direction of anode disk;
v relative velocity between electron beam and focal track in circumferential direction;
cp heat capacity;
µ heat conductivity.

The upper allowed limit of the temperature is the melting temperature of the focal track coating (e.g. 3410° C. for tungsten) or even at a lower temperature to account for thermo mechanical effects ("fatigue").

It was found that relationship (1) may be deduced from the findings in "x-ray anode surface temperatures: the effect of volume heating", Steven Whittaker, SPIE Volume 914, Medical Imaging II, 1988, pp. 565-572. As can be seen the temperature increase is dependent on the relative velocity v between electron beam as it traces out its trajectory and the anode disc 234 in particular a reference point on the focal track FPT as traced out by the beam.

Figure 4A:
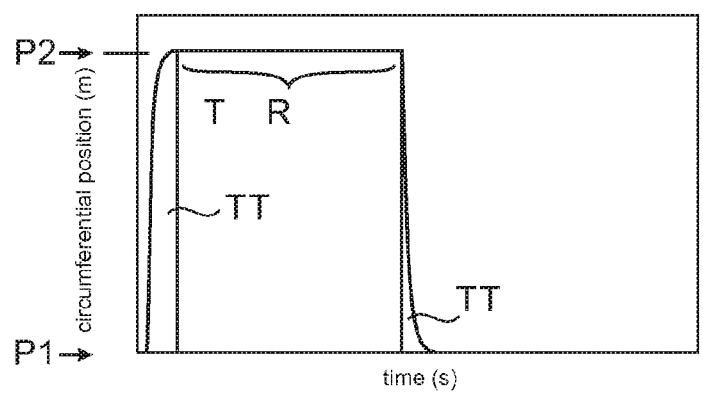
FIGS. 4A-C are graphs showing the timings, positions and velocities involved when controlling operation of x-ray tube of FIG. 2.
Figure 4B:
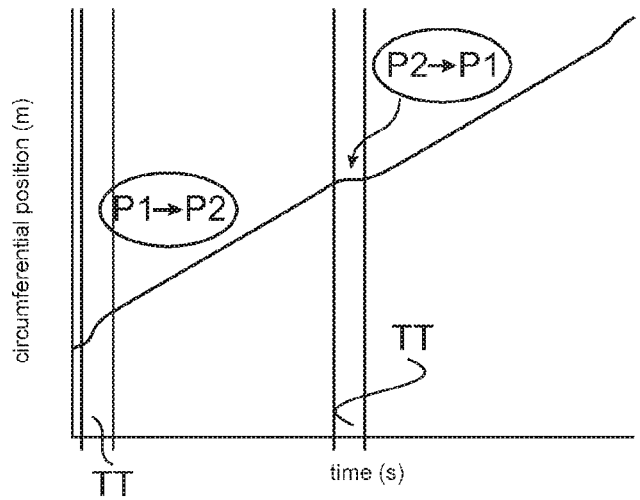
Figure 4C:
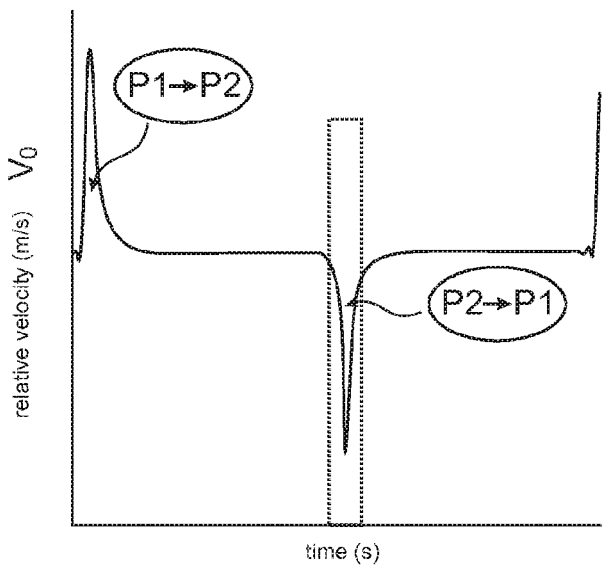

With reference to FIGS. 4A-C, the timing of focal point shift, positions and relative velocity during focal point shift are shown diagrammatically.

FIG. 4A is the transition or shift of focal point FP between rest positions P1 and P2 shown in a rotating coordinate frame relative to P1. Focal point FP initially at rest point P1, shifts ("jumps") during the transition time period TT to the other rest position P2. The transition period TT for FP's jump from position P1 to P2 is in the range of 10 µs (micro-seconds) as compared to the residence time of about 150 µs at position P2 (or P1). A Similar space v time diagram applies for the opposite transition from position P2 to position P1. The circumferential position graphed along the vertical axis is taken on the circumference of the anode disc 234 with rest position P1 as reference point. This is a good approximation because the focal track in one embodiment runs very closely to the outer rim of the anode disc 234. For image reconstruction in CT applications the projection image data are only gathered when the focal spot has reached one of the at least two positions P1, P2. The image data which are gathered during the jumping period (that is, outside the imager's duty cycle) are not used for image reconstruction. Therefore it is the aim to minimize the time needed for jumping between both positions P1, P2. The jump or shift can vary largely and is in the order of 0.01 to 10 mm.

FIG. 4B shows a space v time diagram of focal point FP as it travels across the anode, its motion taken relative to the rest position P1 which is likewise moving due to the anode's motion so the motions are superimposed with the resulting motion taken relative to a fixed coordinate frame relative to an initial position of rest point P1 (but which is itself rotating with the disk). Assuming a rotational velocity at the circumference of the anode disc 234 of about 60 m/s, the graph is a line with constant slope for most of the time except at two "dents" occurring during transition time when the focal point is shifted by the focal point shifter 245/240. With back reference to FIG. 3, the first upward dent at (P1→P2) indicates an increase in velocity so the velocity of focal point trajectory FPT points in a direction opposite to the anode disk 234's rotation. In contrast, at the downward indent (P2→P1) indicates a decrease in velocity so the velocity of focal point trajectory FPT points in rotation direction of anode disk 234 at that instant. In FIG. 4B the jumping function of FIG. 4A is assumed.

In FIG. 4C the relative velocity of the electron beam with respect to the focal point trajectory FPT graphed versus time. In other words, FIG. 4C is the corresponding velocity time diagram of the space time diagram of FIG. 4B. Time instants where velocity components are parallel (P2→P1) or anti-parallel (P1→P2) correspond to velocity downward or upward spikes in FIG. 4C, that is a sharp decrease and increase in relative velocity. As can be seen there is even an instant ("critical period") where the relative velocity is indeed naught (zero crossing) and then increases again albeit in the other direction. A zero crossing in the critical period means that electron beam and anode are stationary with respect to each other. The instant (P2→P1) during focal point shift where the velocity components are aligned in parallel fashion are the critical instants when anode surface temperature can approach melting point of disk material causing the disk to fail earlier than without such high temperature exposure.

In order to avoid or at least contain the sharp temperature increase during focal point shifts where the relative velocity between focal point and anode decreases that is where respective two velocity components are parallel, a controller 210 is provided to help control X-ray tubes 110 operation during focal point shift. Referring back to FIG. 2, controller 210 includes a registering unit 211 and an electron beam mitigator 212.

Broadly speaking, apparatus 210 interfaces focal point controller 245 and is configured to register when a focal point shift occurs. Registering unit 211 interfaces with the respective control channels in controller 245 and listens for a respective triggering signal that is representative for the onset of the focal point shift. Once the respective triggering signal has been registered a corresponding command is issued by registering unit 211 to electron beam mitigator 212 to commence mitigation. Mitigation includes i) blanking out the electron beam during focal shift or ii) partial blanking by reducing power or iii) increasing focal point area. In accordance with the formula above, mitigator 212 compensates for this increase in temperature by either blanking out during the transition time the electron beam or by increasing width and length of the beam's focal point during the transition time. The mitigation action of mitigator 212 is maintained during transition TT.

In other words, focal point registering unit 211 is also configured to listen for signal within focal point controller 245's (or at other suitable points in the circuitry of the tube 110) to learn when the focal point shift has terminated, that is, when the focal point has reached either one of the respective rest points. In one embodiment, if the duration of the focal point shift is known, registering unit 211 listens only for shift commencement signal and mitigator 212's mitigation action ceases upon expiry of a pre-set time interval reflecting the duration of the focal point shift. The registering unit 211's ability to listen for commencement and completion of focal point shift signals can be implemented by using suitable event-driven programming techniques to include in the logic of the registering unit 211 suitably configured event-handlers. Once completion of the focal point shift has been registered a command is issued to mitigator 212 instructing it to cease mitigating action on the electron beam.

According to one embodiment, registering unit 211 monitors the relative velocities of the FP with respect to the focal track points, that is, at the sequence of points where the electron beam impacts or is incident on the anode disk 234. It is the velocity component at those points relative to the velocity components of the focal point FP shift trajectory that is compared. If parallel at that point, a drop in relative velocity occurs which is when the mitigation is triggered should the relative velocity drop below a user-configurable (by way of a suitable UI) threshold.

According to one embodiment, the blanking-out of the electron beam is achieved by means of a grid 250 interposed between anode 230 and cathode 220. Grid 250 is driven by driver 255 and is configured to build up a repellent negative charge to thereby prevent the electrons emitted from cathode 220 to reach anode 230.

In another embodiment and likewise in accordance with the above formula only a "partial" blanking is effected wherein power P delivered from x-ray controller XC to the cathode is reduced during transition time TT. The reduction is proportional to $$\sqrt{v_{xdf}/v_0} \quad (2)$$

where:

$v_{xdf}$ lowest relative velocity of tangential component (parallel to focal track or in rotation direction) during the jump or shift;

$v_0$ average velocity without x-dfs mode ("(d)ynamic (f)ocal (s)pot movement", average velocity when focal point is at rest points or has no velocity components parallel to focal track, so for the case of rotatory disk, has no tangential components in rotation direction). In this way the decrease in relative velocity can just be off-set thereby substantially preventing temperature increase Tfs.

In the embodiment of FIG. 3, right hand side, where the anode rotates and the focal point trajectory FPT is a line tangential to the circular focal track, both quantities $v_{xdf}$ and $v_{xdf}$ are known beforehand so the proportional power reduction factor can be pre-calculated. Same applies for more complex motions when they are known a priori.

In one embodiment, mitigator 212 is configured to effect increasing the focal spot size, that is its extension in radial (length) or a circumferential direction (width), during transitional jumping time. In this embodiment, mitigator 212 instructs beam focus element controller 265 to drive the magnetic focus elements 260 in a defocusing mode. In case of magnetic deflectors, this can be done by the controller 265 delivering short current pulses to the coils of the magnetic elements 260 thereby generating a defocusing magnetic field around the electron beam. In accord with formula (1), a temperature increase during jumping combined with a lower relative velocity is prevented when focal spot length can be increased by a factor of $\sqrt{v_0/v_{xdf}}$ or focal spot width can be increased by a factor of $v_0/v_{xdf}$ or a combination of focal spot length and width increase.

In other words for a focal spot dimension extending radially to the focal spot trajectory an increase proportional to the square root of $v_0/v_{xdf}$ is sufficient whereas for a focal spot dimension extending tangentially to the focal spot trajectory an increase proportional to the ratio $v_0/v_{xdf}$ is sufficient. In either case, the heat developing on the anode surface is spread across a larger region of the anode surface. In yet other words, as the focal point FP's tangential velocity component $v_{xdf}$ decreases, the area or size of said focal point is increased (in other words power density (W/m²) of the electron beam is decreased) by a factor of $\sqrt{v_0/v_{xdf}}$ for the length and/or by a factor of $v_0/v_{xdf}$ for the width.

In one embodiment focal point area increase during transition time period TT has an effect alternative to total or partial blanking of the electron beam. In other embodiments mitigator 212 is user-configurable so the mitigation mode of i) focal point area increase, ii) total blanking, or iii) partial blanking can be selected. In yet other embodiments mode i) may be combined with either one of modes ii) or iii).

In other words, the mitigation action ((partial) blanking out, partial blanking out (the power is reduced) and/or the enlargement of the focal spot size) is synchronized to the frequency and phase of the jumping or leap function shown in FIG. 4A. More particularly, mitigating action of mitigator 212 is synchronized with signals indicative of commencement and signals indicative of completion of the respective shifts ("jumps") between the at least two rest positions P1 and P2 of focal point FP. Of course, in some embodiments focal point trajectory FPT may be defined by more than two rest points P1, P2 outlining a polygon or other shape on the anode disk surface. Mitigating action is maintained for a time period substantially equaling the shifting or jumping time between the respective rest points P1 and P2 of focal point FP. In one embodiment, transition time period is about 10 μs and the mitigation is maintained accordingly for about 10 micro-seconds. It has been observed that sufficient results can be achieved if the mitigation is maintained for a time period of about 10% of the residence time of the electron beam at either one or at least one of the rest positions P1 or P2.

More generally speaking, mitigator 212 is configured to mitigate electron beam during such periods where a velocity component of the focal point trajectory is parallel to a velocity component of the focal point track during focal point shift. In the embodiment shown in FIG. 3, the track FPTR is circular with the trajectory FPT of the focal point shifting along a straight line tangential to the circumference of the disk that is tangential to the focal point track. In this case, the action of the mitigation occurs in every other TT period, that is, only when the focal point shifts in the direction of disk's rotation P2→P1. There is no blanking during the opposite shift P1→P2 because then the relative velocity is increasing so anode temperature is not increasing and the mitigation is skipped in those anti-parallel TT periods. In one embodiment however the blanking may be effected even in each of the transition time TT periods, regardless of whether it is a P1→P2 or a P2→P1 shift. The logic is particularly simple in this case. During each TT, mitigation is activated and maintained during commencement and termination.

When trajectory and anode motion/FP track on anode is known beforehand, the timing of mitigator 212 (active: mitigation, "inactive": no mitigation) can be pre-calculated and the action of registering unit 211 becomes a simple timing on/off the action of mitigator 212.

In other embodiments, mitigator 212 includes a kinetic processor with a sensor suitable to sense each of focal point and anode motions and is configured to calculate from varying focal point trajectories and/or varying focal point tracks (anode motion) the periods during which velocity components are parallel and where a relative velocity drop occurs. In other words, in this embodiment, mitigator 212 allows for adaptive mitigation of the beam in response to changing focal point trajectories and or anode motions.

Mitigator 212 may be arranged as an add-on to existing imagers and may be programmed differently or tailored to each of a plurality of imagers each having different focal point trajectories FPT and/or focal point tracks FPTR. The different timings for active/inactive, can then be calculated/stored individually for each of those imagers. A single control apparatus can then centrally control each of those imagers.

The components of X-ray tube 110 and the components of the control apparatus 210 are shown in FIG. 2 as discrete components spread out in a communication network.

However, this is an exemplary embodiment only. In other embodiments controller 210 is integrated as a software module in the control logic of tube controller XC or in deflector controller 245. The electron beam mitigation functionalities may be provided as subroutines called upon when at branching points during execution of the deflector software when the electron beam jump or shift routines are invoked.

The components of the apparatus are shown as resident on a central computer C and running as software routines in said central computer C. The components may also be arranged as FPGAs or as hardwired standalone chips. The components may be programmed in a suitable scientific computing platform such as Matlab® or Simulink® and then translated into C++ or C routines maintained in a library and linked when called on central computer C.

Figure 5:
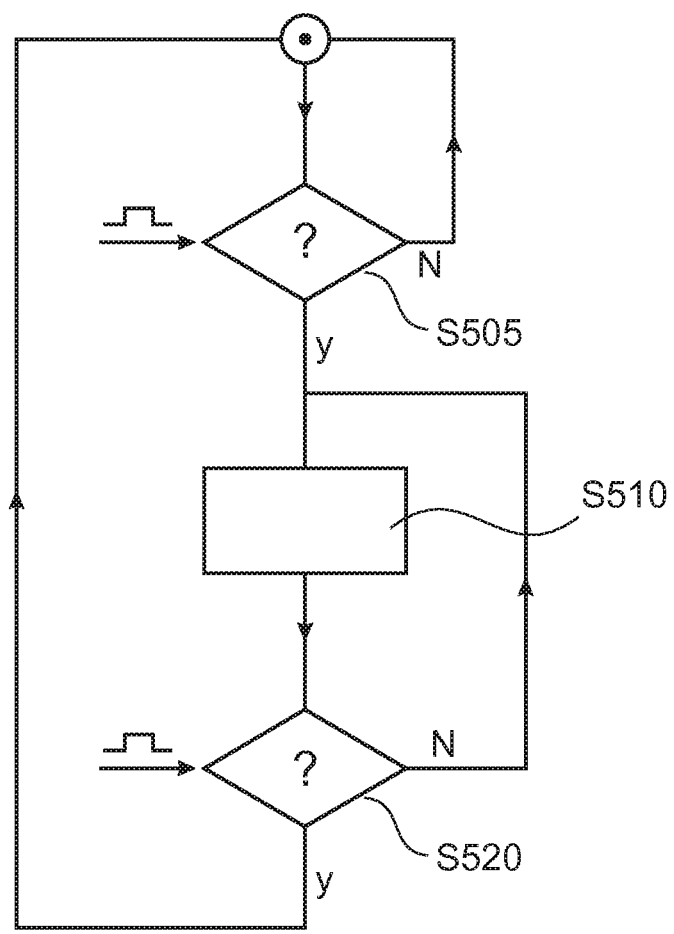
FIG. 5 is a flow chart of the method as proposed herein.

With reference to FIG. 5 a method for controlling x-ray tube with movable anode and shiftable focal point is shown in a flow chart. At Step S505 a focal point shift is registered.

in Step 510 the electron beam is mitigated in response to the focal point shift so registered. The mitigation includes either i) blanking out the electron beam during the shift or ii) partially blanking out the electron beam or iii) increasing the beam's focal spot size during the shift.

At Step S520, once it is registered that the focal point shift is completed, that is, that the focal point has arrived at one of at least two rest positions P1 or P2, electron beam mitigation at step 510 is ceased and flow control returns to Step S505.

Focal point shift or movement can be applied in radial direction of the anode disk, or in circumferential direction of the disk, or both. The focal spot may impinge an outer rim area of the anode disk.

When used in a CT imager, projection image data is only gathered if the focal spot is exactly in one of the at least two rest positions P1, P2, so the jumping time between the two points is as short as possible in comparison to the time the focal spot is located in one of the two desired positions P1, P2. However, if the focal spot when shifting in circumferential direction and in rotation direction, the relative velocity between anode and focal spot drops and may even become zero. As a result of the low or zero relative velocity, the focal track heats up to such high temperatures that X-Ray dose output degrades (due to roughening of anode disk surface at the focal point track) and the risk of arcing increases (due to evaporation in the tube of focal track material). Hence, the tube lifetime is either shorter when relative velocity drops occur or the tube may need to operate with less power. The method according to steps S505-S520 helps reduce above noted disadvantageous effects.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for controlling an X-ray tube with shiftable focal point capability having a movable anode, the focal point formed by an electron beam incident on the anode, the apparatus comprising:
 a focal point shift registering unit for detecting and registering an onset of a focal point shift across the anode, the focal point shift occurring along a trajectory traced out by the shifting focal point across at least part of the moving anode; and an electron beam mitigator configured to mitigate, in response to a command issued by the registering unit upon registering the focal point, the incident electron beam while the shifted focal point traces out the trajectory across the at least part of the moving anode, the mitigation action dependent on relative velocity between the focal point and the anode, wherein the mitigation includes reducing the electron beam power as a function of the square root of a ratio between i) a minimum relative velocity of the focal point during the shift and ii) an average velocity of the anode movement.

2. The apparatus of claim 1, wherein the mitigation commences upon registration by the focal point shift registering unit of a drop in the relative velocity below a threshold value.

3. The apparatus of claim 1, wherein the mitigation remains effective until the relative velocity rebounds to or exceeds the threshold value.

4. The apparatus of claim 1, wherein the electron beam mitigator avoids an increase of temperature at the focal point above a critical temperature threshold while the focal point is shifting.

5. The x-ray tube having an apparatus according to claim 1.

6. An X-ray imager including the X-ray tube according to claim 5.

7. An apparatus for controlling an X-ray tube with shiftable focal point capability having a cathode and a movable anode, the focal point formed by an electron beam incident on the anode, the apparatus comprising:

a focal point shift registering unit for detecting and registering an onset of a focal point shift across the anode, the focal point shift occurring along a trajectory traced out by the shifting focal point across at least part of the moving anode; and an electron beam mitigator configured to mitigate, in response to a command issued by the registering unit upon registering the focal point shift, the incident electron beam while the shifted focal point traces out the trajectory across the at least part of the moving anode, and wherein the trajectory describes an oscillation of the focal point between two rest positions on the anode, the mitigation action remaining effective for as long as the relative velocity is directed in a rotation direction of the anode.

8. The apparatus of claim 7, wherein the mitigation remains effective for 1% to 20% of a residence time of the focal point at either one of the two rest positions.

9. The apparatus of claim 7, wherein the mitigation includes blanking out the electron beam to prevent the electron beam from reaching the anode.

10. The apparatus of claim 9, wherein the blanking out of the electron beam comprises use of a grid interposed between the cathode and the moveable anode.

11. The apparatus of claim 7, wherein the mitigation includes increasing size or area of the focal point.

12. The apparatus of claim 7, wherein the mitigation includes increasing at least one of a length of the focal point perpendicular to the focal point track and a width of the focal point along the focal point track, as a function of a ratio or the square root of the ratio between i) the average velocity of the anode movement and ii) a minimum relative velocity of the focal point during the shift.

13. A method of controlling an X-ray tube with shiftable focal point capability having a movable anode, the focal point formed by an electron beam incident on the anode, the method comprising:

registering a focal point shift across the anode, the shift occurring along a trajectory traced out by the shifting focal point across at least part of the moving anode;

mitigating, in response to the focal point shift being registered, the incident electron beam while shifted focal point traces out the trajectory across the moving anode, the mitigation depending on a relative velocity between the focal point and the anode, wherein the mitigation includes reducing the electron beam power as a function of the square root of the ratio between i) the minimum relative velocity of the focal point during the shift and ii) the average velocity of the anode movement.

14. A computer program element, executable by a processing unit, adapted to perform the method of claim 13.

15. A computer readable medium storing the computer program element of claim 14.

* * * * *